(12) United States Patent
Okabe et al.

(10) Patent No.: US 9,170,196 B2
(45) Date of Patent: Oct. 27, 2015

(54) OPTICAL MEASURING DEVICE

(71) Applicant: MITUTOYO CORPORATION, Kawasaki-shi, Kanagawa (JP)

(72) Inventors: Kenji Okabe, Kawasaki (JP); Tatsuya Nagahama, Kawasaki (JP); Nobuya Kaneko, Kawasaki (JP)

(73) Assignee: MITUTOYO CORPORATION, Kawasaki (JP)

( * ) Notice: Subject to any disclaimer, the term of this patent is extended or adjusted under 35 U.S.C. 154(b) by 0 days.

(21) Appl. No.: 14/167,562

(22) Filed: Jan. 29, 2014

(65) Prior Publication Data

US 2014/0145084 A1    May 29, 2014

Related U.S. Application Data

(62) Division of application No. 13/305,038, filed on Nov. 28, 2011.

(30) Foreign Application Priority Data

Dec. 17, 2010  (JP) ................. 2010-281102

(51) Int. Cl.
*G01N 21/64*   (2006.01)
*G02B 21/24*   (2006.01)
*G01N 21/25*   (2006.01)

(52) U.S. Cl.
CPC ............. *G01N 21/64* (2013.01); *G01N 21/25* (2013.01); *G02B 21/248* (2013.01)

(58) Field of Classification Search
CPC .... G02B 21/00; G02B 21/0032; G02B 21/02; G02B 21/025; G02B 21/248; G02B 5/20; G02B 5/22; G02B 5/28; G01N 21/64; G01N 21/25
See application file for complete search history.

(56) References Cited

U.S. PATENT DOCUMENTS 5,585,964 A    12/1996 Schalz
5,827,190 A    10/1998 Palcic et al.
(Continued)

FOREIGN PATENT DOCUMENTS

CN    1415267 A    5/2003
CN    1724997 A    1/2006
(Continued)

OTHER PUBLICATIONS

Oct. 30, 2014 Office Action issued in U.S. Appl. No. 13/305,038.
(Continued)

*Primary Examiner* — Yara B Green
(74) *Attorney, Agent, or Firm* — Oliff PLC

(57) ABSTRACT

In an optical measuring device, the visual observation section includes: a white light source which emits white light; a first objective lens arranged between the white light source and measurement object, through which the white light emitted from the white light source and return light from the measurement object transmit; a plurality of tube lenses which change a magnification of the return light passing through the first objective lens to a predetermined magnification; and a lens switching mechanism which can selectively switch the tube lenses so as to select one of the tube lenses to be arranged on the return light, and the special observation section includes: a special light source which emits special light; and a second objective lens arranged between the special light source and measurement object, through which the special light emitted from the special light source and return light from the measurement object transmit.

6 Claims, 11 Drawing Sheets

(56) References Cited

U.S. PATENT DOCUMENTS

| | | |
|---|---|---|
| 6,400,395 B1 | 6/2002 | Hoover et al. |
| 6,525,874 B2 * | 2/2003 | Yamawaki .................. 359/361 |
| 6,650,357 B1 | 11/2003 | Richardson |
| 7,075,714 B2 | 7/2006 | Yonetani et al. |
| 2003/0078477 A1 | 4/2003 | Kang et al. |
| 2009/0121154 A1 * | 5/2009 | Westphal et al. .......... 250/484.4 |
| 2010/0133417 A1 | 6/2010 | Nagahama et al. |
| 2013/0182096 A1 * | 7/2013 | Boccara et al. ................ 348/79 |

FOREIGN PATENT DOCUMENTS

| | | |
|---|---|---|
| CN | 101401722 A | 4/2009 |
| CN | 101750712 A | 6/2010 |
| EP | 1 207 387 A1 | 5/2002 |
| EP | 1 403 675 A2 | 3/2004 |
| JP | A-09-304682 | 11/1997 |
| JP | A-2010-190776 | 9/2010 |

OTHER PUBLICATIONS

Jan. 24, 2014 Notification of First Office Action issued in Chinese Application No. 201110423282.2 with English-language translation.

Feb. 20, 2014 Notification of Grounds for Rejection issued in Korean Application No. 10-2011-0135683 with English-language translation.

May 6, 2014 Office Action issued in U.S. Appl. No. 13/305,038.

Apr. 8, 2014 Notification of Reasons for Refusal issued in Japanese Patent Application No. 2010-281102 with English-language translation.

Sep. 26, 2014 Notification of the Second Office Action issued in Chinese Patent Application No. 201110423282.2 (with English translation).

* cited by examiner

OPTICAL MEASURING DEVICE

BACKGROUND OF THE INVENTION

1. Field of the Invention

This application is a division of U.S. application Ser. No. 13/305,038, filed Nov. 28, 2011, and claims priority to Japanese Patent Application No. 2010-281102, filed on Dec. 17, 2010. The prior applications, including the specifications, drawings and abstracts are incorporated herein by reference in their entirety.

2. Description of Related Art

There has conventionally been known an optical measuring device including a power turret which can turn to switch a plurality of tube lenses each having a different magnification so as to select one of them, whereby magnification can easily be changed. With this configuration, the optical measuring device can be used for a visual observation of various measurement objects (workpieces) (see Japanese Patent No. 3363703, for example).

In a conventional optical measuring device 7, as illustrated in FIG. 7 for example, white light emitted from a white light source 710 passes through an objective lens 740 through a mirror 720 and a beam splitter 730 so that a workpiece W is irradiated with the white light. The white light with which the workpiece W is irradiated is reflected on a surface of the workpiece W, passes through one (a tube lens 750A in the figure) of a plurality of tube lenses 750 (750A, 750B, 750C), which is selectively switched by a power turret 760, via the objective lens 740 and the beam splitter 730, and enters a charge coupled device (CCD) camera 770. The conventional optical measuring device 7 observes an image of the workpiece W with the above-mentioned configuration.

Recently, there has been increased a demand for various observations and measurements, such as an observation of a wiring covered with a silicon or film, and an observation of a wiring covered by a resin film such as a solder resist formed on an integrated circuit (IC) wafer. However, the optical measuring device described above has a problem of having difficulty in observing the wiring, because the irradiated light is reflected on the surface of the workpiece W (i.e., is reflected before it reaches the wiring).

In order to solve the above-mentioned problem, there has been known a device which can perform a special observation such as a near-infrared observation and fluorescent observation, for example.

The near-infrared observation is an observation to be performed through a substance, through which near infrared light transmits, by utilizing a property of the near infrared light. Such property includes a property of having a longer wavelength than that of a visible light, a property of being invisible to naked eyes, and a property of passing through a thin material such as silicon and a film, and a skin tissue, differently from the visible light.

Examples of main usages of the near-infrared observation include an inspection of a circuit board using a thin material such as silicon and a film, and a vein authentication to be utilized for security.

As illustrated in FIG. 8, a conventional optical measuring device 8 for a near-infrared observation employs a special light source 810 which emits only near infrared light, such as a near-infrared light-emitting diode (LED) light source, and allows the near infrared light emitted from the special light source 810 to pass through an objective lens 840 via a mirror 820 and a beam splitter 830, so that the workpiece W is irradiated with the near infrared light. The near infrared light with which the workpiece W is irradiated passes through a surface of the workpiece W and is reflected on a not-illustrated wiring, passes through a tube lens 850 via the objective lens 840 and the beam splitter 830, and enters a CCD camera 860. The optical measuring device 8 for the near-infrared observation observes an image of the wiring inside the workpiece W with the above-mentioned configuration.

Meanwhile, the fluorescent observation is to irradiate a workpiece with excitation light corresponding to the workpiece, and to observe fluorescence emitted from the workpiece. Specifically, the fluorescent observation is to observe the wiring inside the workpiece by utilizing a phenomenon in which, after the light (excitation light) with which the workpiece is irradiated is absorbed by a pigment molecule of a fluorescent material formed on the surface of the workpiece, the fluorescent material emits light (fluorescence) according to a thickness of the fluorescent material. Since the thickness of the fluorescent material covering the wiring varies according to a structure of the wiring, the structure of the wiring can be found by observing an intensity of the fluorescence emitted from the fluorescent material. Here, the fluorescent material means a material which emits fluorescence, and includes a wide variety of materials. Thus, the excitation light corresponding to each fluorescent material and the wavelength of the fluorescence emitted from each fluorescent material are varied.

Examples of main usages of the fluorescent observation include an inspection of an IC wafer using a solder resist, and an observation of a biological tissue or cell stained with a fluorescent pigment.

As illustrated in FIG. 9, a conventional optical measuring device 9 for a fluorescent observation employs a special light source 910 which emits only excitation light, and provides an excitation filter 920, through which only excitation light having a wavelength corresponding to a workpiece W transmits, on an optical axis of the excitation light emitted from the special light source 910. With this configuration, the excitation light corresponding to the workpiece W is obtained, and the obtained excitation light transmits through an objective lens 950 via a mirror 930 and a dichroic mirror 940, so that the workpiece W is irradiated with the excitation light. Then, the fluorescence according to the thickness of the fluorescent material formed on the workpiece W is emitted from the workpiece W irradiated with the excitation light, and the excitation light is reflected on the workpiece W. The fluorescence and the excitation light from the workpiece W pass through a fluorescence filter 970, through which only fluorescence transmits, via the objective lens 950 and the dichroic mirror 940. The fluorescence passing through the fluorescence filter 970 passes through a tube lens 960 to enter a CCD camera 980. The conventional optical measuring device 9 for the fluorescent observation observes an image of the wiring inside the workpiece W with the above-mentioned configuration.

However, in the case of the configuration where the workpiece is irradiated with only the near infrared light, such as the above-mentioned optical measuring device for the near-infrared observation, the ordinary visual observation requiring irradiation of the workpiece W with the white light cannot be performed.

Similarly, in the case of the configuration where the workpiece is irradiated with only the excitation light corresponding to the workpiece, such as the above-mentioned optical measuring device for the fluorescent observation, the ordinary visual observation requiring irradiation of the workpiece W with the white light cannot be performed.

SUMMARY OF THE INVENTION

The object of the present invention is to provide an optical measuring device which can make not only a visual observation but also a special observation such as a near-infrared observation and fluorescent observation to a measurement object.

According to a first aspect of the present invention, there is provided an optical measuring device including: a visual observation section for performing a visual observation of a measurement object; and a special observation section for performing a special observation of the measurement object, wherein the visual observation section includes: a white light source which emits white light; a first objective lens arranged between the white light source and the measurement object, through which lens the white light emitted from the white light source and return light from the measurement object transmit; a plurality of tube lenses which change a magnification of the return light passing through the first objective lens to a predetermined magnification; and a lens switching mechanism which can selectively switch the tube lenses so as to select one of the tube lenses which is to be arranged on the return light, and wherein the special observation section includes: a special light source which emits special light; and a second objective lens arranged between the special light source and the measurement object, through which lens the special light emitted from the special light source and return light from the measurement object transmit.

According to a second aspect of the present invention, there is provided an optical measuring device including: a white light source which emits white light including special light; an objective lens arranged between the white light source and a measurement object, through which lens the white light emitted from the white light source and return light from the measurement object transmit; a plurality of tube lenses which change a magnification of the return light passing through the objective lens to a predetermined magnification; a special filter provided on one of the tube lenses, through which filter only predetermined light transmits; and a lens switching mechanism which can selectively switch the tube lenses so as to select one of the tube lenses which is to be arranged on the return light.

BRIEF DESCRIPTION OF THE DRAWINGS

The present invention will become more fully understood from the detailed description given hereinbelow and the appended drawings which given by way of illustration only, and thus are not intended as a definition of the limits of the present invention, and wherein.

DETAILED DESCRIPTION OF THE INVENTION

An optical measuring device according to the present invention will be described in detail with reference to the drawings. The optical measuring device according to the present invention is mounted to an optical apparatus such as a microscope, image measuring device, etc., for example.

(First Embodiment)

A configuration will firstly be described.

Figure 1:
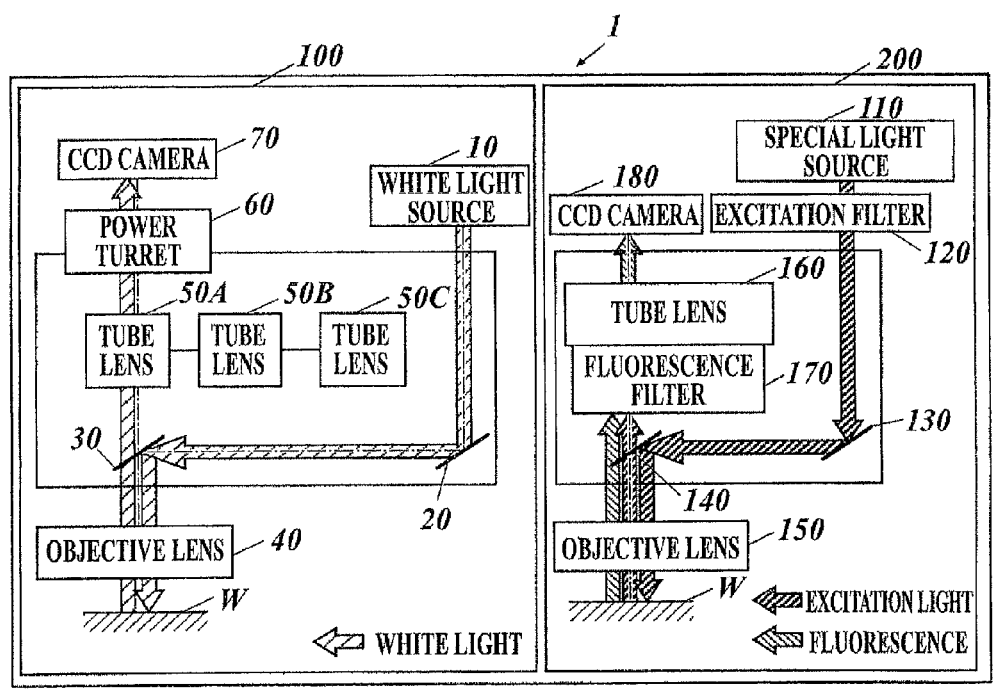
FIG. 1 is a schematic view illustrating a configuration of an optical measuring device according to a first embodiment.

An optical measuring device 1 according to a first embodiment includes a visual observation section 100 for visually observing a workpiece W, and a fluorescent observation section 200 serving as a special observation section for a fluorescent observation of the workpiece W, as illustrated in FIG. 1.

The visual observation section 100 includes a white light source 10, a mirror 20, a beam splitter 30, an objective lens 40, tube lenses 50A, 50B, and 50C, a power turret 60, and a CCD camera 70.

The white light source 10 is composed of a halogen, discharge lamp, or light-emitting diode, for example, and generates and emits white light. With the white light emitted from the white light source 10, the mirror 20 arranged below the white light source 10 in the vertical direction is irradiated.

The mirror 20 reflects the white light, irradiated from the white light source 10, toward the beam splitter 30 arranged at the left side in the horizontal direction. With the white light reflected by the mirror 20, the beam splitter 30 is irradiated from the right side in the horizontal direction.

The beam splitter 30 reflects the white light irradiated from the mirror 20 toward the objective lens 40 arranged below in the vertical direction. The white light reflected by the beam splitter 30 enters the objective lens 40 from above in the vertical direction.

Return light, which is reflected on the surface of the workpiece W and passes through the objective lens 40 from below in the vertical direction, transmits through the beam splitter 30. The return light passing through the beam splitter 30 enters the tube lens 50 (the tube lens 50A in the figure) arranged above in the vertical direction.

The objective lens 40 is mounted so as to be opposite to the workpiece W. The white light entering from the beam splitter 30 transmits through the objective lens 40. With the white light passing through the objective lens 40, the workpiece W is irradiated from above in the vertical direction.

Return light, which is reflected on the surface (inner surface) of the workpiece W, transmits through the objective lens 40. With the return light passing through the objective lens 40, the beam splitter 30 arranged above in the vertical direction is irradiated.

Specifically, the objective lens 40 is arranged between the white light source 10 and the workpiece W, and the white light emitted from the white light source 10 and the return light from the workpiece W transmit through the objective lens 40.

The tube lenses 50 (50A, 50B, 50C) are three optical lenses, each having a different magnification, for example, wherein one (the tube lens 50A in the figure) of the tube lenses 50 is arranged on the return light entering from the beam splitter 30 so as to change a magnification of the return light to a predetermined magnification, and to allow the same to transmit therethrough. The return light passing through the tube lens 50 enters the CCD camera 70 arranged above in the vertical direction through the power turret 60.

The number of the tube lenses 50 is not limited to three, and any number not less than 2 may be adopted.

The power turret 60 is a turret, for example, which is provided so as to be rotatable about an axis as a center, which axis is at a position different from that of the return light from the workpiece W and parallel to the return light. The power turret 60 includes the three tube lenses 50A, 50B, and 50C mounted thereon at equal spaces (space of 120 degrees) on a circumference having a radius which is the distance from the axis to the return light.

Specifically, the power turret 60 serves as a lens switching mechanism which can selectively switch the tube lenses 50 (50A, 50B, 50C) to select one of them which is to be arranged on the return light.

The CCD camera 70 is an image sensor which captures an image of the workpiece W based upon the return light from the workpiece W so as to acquire image data. The acquired image data is output to a not-illustrated control section which performs various image processes, and the like.

The fluorescent observation section 200 includes a special light source 110, an excitation filter 120, a mirror 130, a dichroic mirror 140, an objective lens 150, a tube lens 160, a fluorescence filter 170, and a CCD camera 180.

The special light source 110 is composed of a halogen, discharge lamp, or light-emitting diode, for example, and generates and emits excitation light. With the excitation light emitted from the special light source 110, the excitation filter 120 arranged below the special light source 110 in the vertical direction is irradiated.

The excitation filter 120 is a filter through which only excitation light having a wavelength for making the fluorescence emitted from the workpiece W transmits.

Specifically, the excitation filter 120 is arranged between the special light source 110 and the workpiece W, and only the excitation light having a wavelength for making the fluorescence emitted from the workpiece W, out of the excitation light entering from the special light source 110, transmits through the excitation filter 120, so that the mirror 130 arranged below in the vertical direction is irradiated.

The mirror 130 reflects the excitation light, passing through the excitation filter 120, toward the dichroic mirror 140 arranged at the left side in the horizontal direction. With the excitation light reflected from the mirror 130, the dichroic mirror 140 is irradiated from the right side in the horizontal direction.

The dichroic mirror 140 reflects the excitation light irradiated from the mirror 130 toward the objective lens 150 arranged below in the vertical direction. The excitation light reflected from the dichroic mirror 140 enters the objective lens 150 from above in the vertical direction.

Return light which passes through the objective lens 150 from below in the vertical direction transmits through the dichroic mirror 140. With the return light passing through the dichroic mirror 140, the fluorescence filter 170 arranged above in the vertical direction is irradiated.

The objective lens 150 is mounted to be opposite to the workpiece W. The excitation light entering from the dichroic mirror 140 transmits through the objective lens 150. With the excitation light passing through the objective lens 150, the workpiece W is irradiated from above in the vertical direction.

The excitation light reflected on the workpiece W, and the return light composed of fluorescence and emitted from a fluorescent material formed on the workpiece W, transmit through the objective lens 150. With the return light passing through the objective lens 150, the dichroic mirror 140 arranged above in the vertical direction is irradiated.

Specifically, the objective lens 150 is arranged between the special light source 110 and the workpiece W, and allows the excitation light passing through the excitation filter 120, out of the excitation light emitted from the special light source 110, and the return light from the workpiece W, to transmit the objective lens 150.

The fluorescence filter 170 is a filter through which only fluorescence transmits.

Specifically, only the fluorescence emitted from the workpiece W, out of the return light passing through the dichroic mirror 140, transmits through the fluorescence filter 170.

The tube lens 160 changes a magnification of the fluorescence passing through the fluorescence filter 170 to a predetermined magnification and allows the same to transmit through the tube lens 160. The fluorescence passing through the tube lens 160 enters the CCD camera 180 arranged above in the vertical direction.

The CCD camera 180 is an image sensor which captures an image of the workpiece W based upon the return light from the workpiece W so as to acquire image data. The acquired image data is output to a not-illustrated control section which performs various image processes, and the like.

An operation will next be described.

In the visual observation section 100 of the optical measuring device 1, the white light emitted from the white light source 10 passes through the objective lens 40 via the mirror 20 and the beam splitter 30 so that the workpiece W is irradiated with the white light. The white light with which the workpiece W is irradiated reflected on the surface of the workpiece W, and passes through one (the tube lens 50A in the figure) of the tube lenses 50 (50A, 50B, 50C), which is selectively switched by the power turret 60, via the objective lens 40 and the beam splitter 30, thereby entering the CCD camera 70.

In the fluorescent observation section 200 of the optical measuring device 1, the special light source 110 which emits only excitation light is used, and the excitation filter 120 through which only the excitation light having a wavelength corresponding to the workpiece W transmits is arranged on the optical axis of the excitation light emitted from the special light source 110. With this structure, the excitation light corresponding to the workpiece W can be obtained. The obtained excitation light passes through the objective lens 150 via the mirror 130 and the dichroic mirror 140, thereby the workpiece W is irradiated with the excitation light. On the workpiece W irradiated with the excitation light, the fluorescence according to the thickness of the fluorescent material formed on the workpiece W is emitted, and the irradiated excitation light is reflected. The return light including the fluorescence and the excitation light from the workpiece W passes through the fluorescence filter 170, through which only the fluorescence transmits, via the objective lens 150 and the dichroic mirror 140. The fluorescence passing through the fluorescence filter 170 passes through the tube lens 160, and enters the CCD camera 180.

The objective lens 40 and the objective lens 150 can be moved integrally in the horizontal direction, whereby one of them can be made opposite to the workpiece W depending upon the intended use.

Specifically, when the visual observation is performed, the objective lens 40 is moved to the position opposite to the workpiece W, while the objective lens 150 is moved to the position opposite to the workpiece W when the fluorescent observation is performed. With this operation, the observation method can easily be changed.

As described above, the optical measuring device 1 according to the first embodiment includes the visual observation section 100 for performing the visual observation of the workpiece W, and the special observation section (fluorescent observation section 200) for performing the special observation of the workpiece W, wherein the visual observation section 100 includes the white light source 10 which emits white light, the objective lens 40 which is arranged between the white light source 10 and the workpiece W and allows the white light emitted from the white light source 10 and the return light from the workpiece W to transmit through the objective lens 40, the tube lenses 50 (50A, 50B, 50C) which change the magnification of the return light passing through the objective lens 40 to a predetermined magnification, and the power turret 60 which can selectively switch the tube lenses 50 to select one of them which is to be arranged on the return light, and wherein the special observation section includes the special light source 110 which emits special light, and the objective lens 150 which is arranged between the special light source 110 and the workpiece W and allows the special light emitted from the special light source 110 and the return light from the workpiece W to transmit the objective lens 150.

With this configuration, the visual observation and special observation can be performed to the workpiece W, which means that the observation method can easily be changed depending upon the use intended by a user.

Particularly, the optical measuring device 1 according to the first embodiment further includes the excitation filter 120 which is arranged between the special light source 110 and the objective lens 150 for allowing only the passage of the excitation light having the wavelength for making the fluorescence emitted from the workpiece W, and the fluorescence filter 170 which allows only the passage of the fluorescence emitted from the workpiece W out of the return light passing through the objective lens 150, wherein the special light is the excitation light, and the objective lens 150 allows the excitation light passing through the excitation filter 120 out of the excitation light emitted from the special light source 110 to transmit through the objective lens 150.

With this configuration, not only the visual observation but also the fluorescent observation can be performed to the workpiece W. Therefore, an IC wafer using a solder resist can be inspected, and a biological tissue or cell stained with a fluorescent pigment can be observed, for example.

(Second Embodiment)

A configuration will firstly be described. For simplifying the description, the components same as those in the first embodiment are denoted by the same numerals, and the description will not be repeated.

Figure 2:
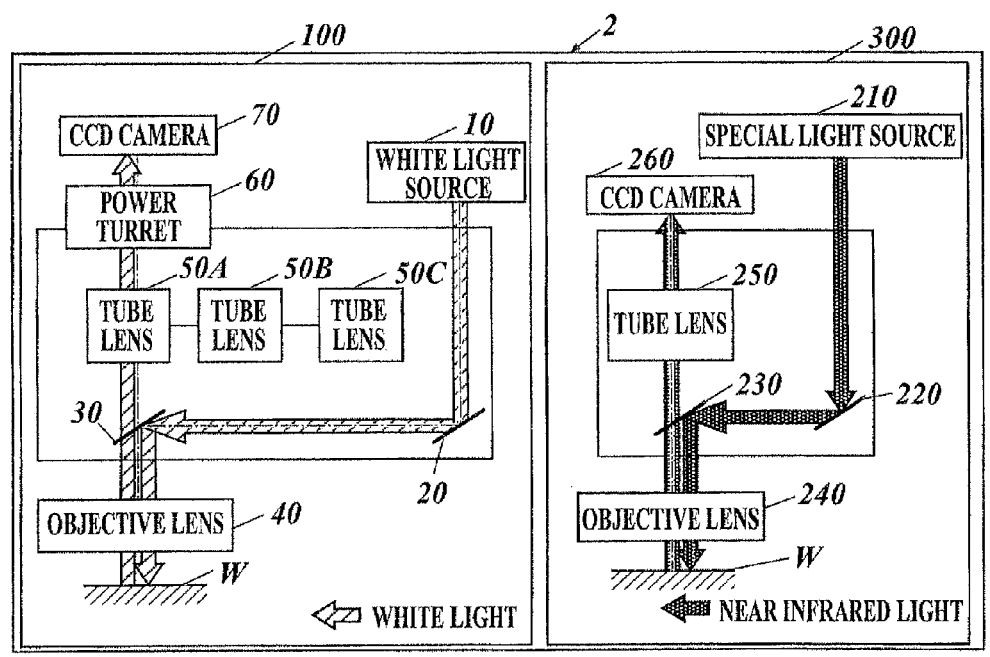
FIG. 2 is a schematic view illustrating a configuration of an optical measuring device according to a second embodiment.

An optical measuring device 2 according to a second embodiment includes a visual observation section 100 for visually observing a workpiece W, and a near-infrared observation section 300 serving as a special observation section for a near-infrared observation of the workpiece W, as illustrated in FIG. 2.

The near-infrared observation section 300 includes a special light source 210, a mirror 220, a beam splitter 230, an objective lens 240, a tube lens 250, and a CCD camera 260.

The special light source 210 is composed of a halogen, discharge lamp, or light-emitting diode, for example, and it generates and emits near infrared light. With the near infrared light emitted from the special light source 210, the mirror 220 arranged below the special light source 210 in the vertical direction is irradiated.

The mirror 220 reflects the near infrared light, irradiated from the special light source 210, toward the beam splitter 230 arranged at the left side in the horizontal direction. With the near infrared light reflected by the mirror 220, the beam splitter 230 is irradiated from the right side in the horizontal direction.

The beam splitter 230 reflects the near infrared light irradiated from the mirror 220 toward the objective lens 240 arranged below in the vertical direction. The near infrared light reflected by the beam splitter 230 enters the objective lens 240 from above in the vertical direction.

Return light, which passes through the surface of the workpiece W is reflected by a not-illustrated wiring, passes through the objective lens 240 from below in the vertical direction, and transmits through the beam splitter 230. The return light passing through the beam splitter 230 enters the tube lens 250 arranged above in the vertical direction.

The objective lens 240 is mounted to be opposite to the workpiece W. The near infrared light entering from the beam splitter 230 transmits through the objective lens 240. With the near infrared light passing through the objective lens 240, the workpiece W is irradiated from above in the vertical direction.

Return light, which passes through the surface of the workpiece W and is reflected by the not-illustrated wiring, transmits through the objective lens 240. With the return light passing through the objective lens 240, the beam splitter 230 arranged above in the vertical direction is irradiated.

Specifically, the objective lens 240 is arranged between the special light source 210 and the workpiece W, and allows the near infrared light emitted from the special light source 210 and the return light from the workpiece W to transmit through the objective lens 240.

The tube lens 250 changes a magnification of the return light entering from the beam splitter 230, to a predetermined magnification, and allows the same to transmit through the tube lens 250. The return light passing through the tube lens 250 enters the CCD camera 260 arranged above in the vertical direction.

The CCD camera 260 is an image sensor which captures an image of the workpiece W based upon the return light from the workpiece W so as to acquire image data. The acquired image data is output to a not-illustrated control section which performs various image processes, and the like.

An operation will next be described.

In the visual observation section 100 of the optical measuring device 2, the white light emitted from the white light source 10 passes through the objective lens 40 via the mirror 20 and the beam splitter 30 so that the workpiece W is irradiated with the white light. The white light with which the workpiece W is irradiated is reflected on the surface of the workpiece W, and passes through one (the tube lens 50A in the figure) of the tube lenses 50 (50A, 50B, 50C), which is selectively switched by the power turret 60, via the objective lens 40 and the beam splitter 30, thereby entering the CCD camera 70.

In the near-infrared observation section 300 of the optical measuring device 2, the special light source 210 which emits only near infrared light is used, wherein the near infrared light emitted from the special light source 210 is transmitted through the objective lens 240 via the mirror 220 and the beam splitter 230 so that the workpiece W is irradiated with the near infrared light. The near infrared light, with which the workpiece W is irradiated, passes through the surface of the workpiece W and is reflected by the not-illustrated wiring, and passes through the tube lens 250 via the objective lens 240 and the beam splitter 230, thereby entering the CCD camera 260.

The objective lens 40 and the objective lens 240 can be moved integrally in the horizontal direction, whereby one of them can be made opposite to the workpiece W depending upon the intended use.

Specifically, when the visual observation is performed, the objective lens 40 is moved to the position opposite to the workpiece W, while the objective lens 240 is moved to the position opposite to the workpiece W when the near-infrared observation is performed. With this operation, the observation method can easily be changed.

As described above, the optical measuring device 2 according to the second embodiment employs the light source, which emits near infrared light, as the special light source 210. Therefore, not only the visual observation at the visual observation section 100 but also the near-infrared observation at the special observation section (near-infrared observation section 300) can be performed to the workpiece W. Accordingly, a circuit board using a thin material such as a silicon or film can be inspected, and a vein authentication to be utilized for security can be performed, for example.

(Third Embodiment)

A configuration will firstly be described. For simplifying the description, the components same as those in the first and second embodiments are denoted by the same numerals, and the description will not be repeated.

Figure 3:
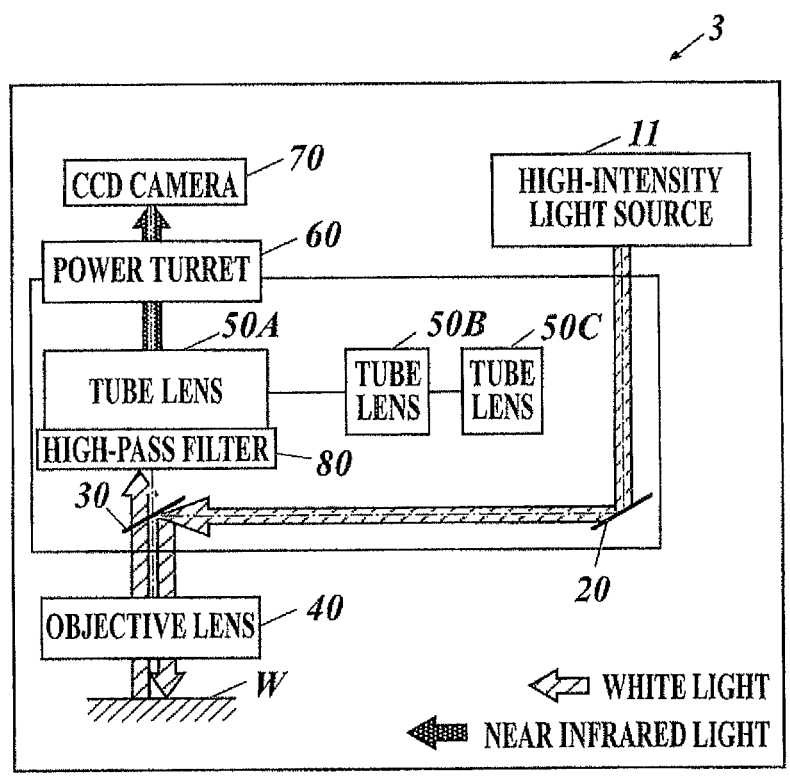
FIG. 3 is a schematic view illustrating a configuration of an optical measuring device according to a third embodiment.

An optical measuring device 3 according to a third embodiment includes, as illustrated in FIG. 3, a high-intensity light source 11, a mirror 20, a beam splitter 30, an objective lens 40, tube lenses 50A, 50B, and 50C, a high-pass filter 80, a power turret 60, and a CCD camera 70.

The high-intensity light source 11 is a wideband light source composed of a halogen, discharge lamp, or light-emitting diode, for example, and generates and emits high-intensity white light including near infrared light. With the white light emitted from the high-intensity light source 11, the mirror 20 arranged below the high-intensity light source 11 in the vertical direction is irradiated.

The high-pass filter 80 is a filter through which only near infrared light transmits.

Specifically, only the near infrared light out of the return light (white light including the near infrared light) passing through the beam splitter 30 transmits through the high-pass filter 80.

The high-pass filter 80 is provided so as to be integral with one (the tube lens 50A in the figure) of the tube lenses 50 (50A, 50B, 50C), and moves with the switching operation of the tube lens 50 by the power turret 60.

An operation will next be described.

In the optical measuring device 3, the high-intensity white light, which is emitted from the high-intensity light source 11 and includes the near infrared light, passes through the objective lens 40 via the mirror 20 and the beam splitter 30 so that the workpiece W is irradiated with the high-intensity white light. The near infrared light included in the white light with which the workpiece W is irradiated passes through the surface of the workpiece W, and is reflected by the not-illustrated wiring. The return light from the workpiece W passes through the high-pass filter 80, through which only the near infrared light transmits, via the objective lens 40 and the beam splitter 30. The near infrared light passing through the high-pass filter 80 passes through the tube lens 50A so that the CCD camera 70 is irradiated with the near infrared light.

On the other hand, when the tube lens 50 (for example, the tube lens 50B) having no high-pass filter 80 provided thereon is arranged on the return light by the switching operation of the tube lens 50 by the power turret 60, the return light from the workpiece W passes through the tube lens 50B to enter the CCD camera 70 as unchanged, since the high-pass filter 80 is not present on the return light.

As described above, the optical measuring device 3 according to the third embodiment includes the white light source (high-intensity light source 11) which emits white light including special light, the objective lens 40 which is arranged between the high-intensity light source 11 and the workpiece W for allowing the passage of the white light emitted from the high-intensity light source 11 and the return light from the workpiece W, the tube lenses 50 (50A, 50B, 50C) which change the magnification of the return light passing through the objective lens 40 to a predetermined magnification, a special filter (high-pass filter 80) which is provided to one (for example, the tube lens 50A) of the tube lenses 50 and through which only a predetermined light transmits, and a power turret 60 which can selectively switch the tube lenses 50 to select one of them which is to be arranged on the return light.

With this configuration, whether the special filter is arranged on the return light from the workpiece W or not can be selected by switching operation of the tube lens 50 by the power turret 60. Therefore, a user can easily make a changeover between the visual observation and the special observation.

Especially, the optical measuring device 3 according to the third embodiment employs the light source which emits white light including the near infrared light as the white light source, and the high-pass filter 80 through which only the near infrared light transmits as the special filter. Therefore, not only the visual observation but also the near-infrared observation can be made according to switching operation of the tube lens 50 by the power turret 60. Accordingly, a circuit board using a thin material such as silicon and a film can be inspected, and a vein authentication to be utilized for security can be performed, for example.

(Fourth Embodiment)

A configuration will firstly be described. For simplifying the description, the components same as those in the first to third embodiments are denoted by the same numerals, and the description will not be repeated.

Figure 4:
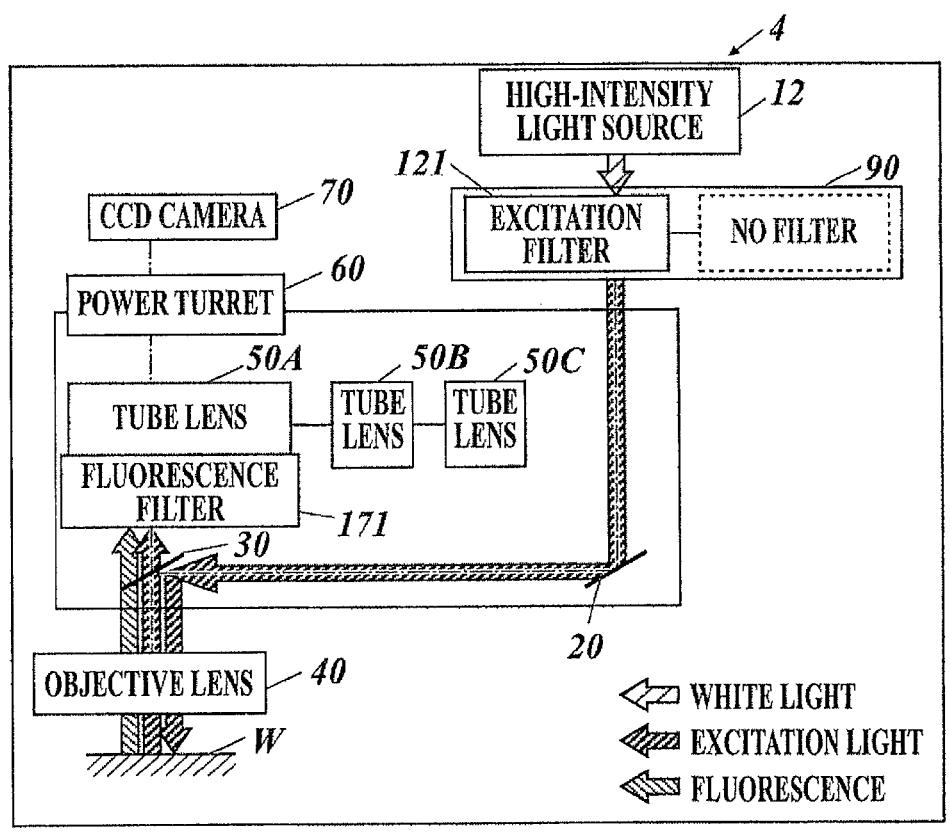
FIG. 4 is a schematic view illustrating a configuration of an optical measuring device according to a fourth embodiment.

An optical measuring device 4 according to a fourth embodiment includes, as illustrated in FIG. 4, a high-intensity light source 12, a filter-switching turret 90, a mirror 20, a beam splitter 30, an objective lens 40, tube lenses 50A, 50B, and 50C, a fluorescence filter 171, a power turret 60, and a CCD camera 70.

The high-intensity light source 12 is a wideband light source composed of a halogen, discharge lamp, or light-emitting diode, for example, and generates and emits high-intensity white light including excitation light. With the white light emitted from the high-intensity light source 12, the filter-switching turret 90 arranged below the high-intensity light source 12 in the vertical direction is irradiated.

The filter-switching turret 90 is a turret which can selectively make a changeover as to whether the excitation filter 121, through which only excitation light having a wavelength for making the fluorescence emitted from the workpiece W transmits, is arranged on the white light emitted from the high-intensity light source 12 or not. It serves as a filter-switching mechanism.

The fluorescence filter 171 is a filter through which only fluorescence transmits.

Specifically, only the fluorescence emitted from the workpiece W, out of the return light passing through the beam splitter 30, transmits through the fluorescence filter 171.

The fluorescence filter 171 is provided so as to be integral with one (the tube lens 50A in the figure) of the tube lenses 50

(50A, 50B, 50C), and moves with the switching operation of the tube lens 50 by the power turret 60.

An operation will next be described.

The optical measuring device 4 has the filter-switching turret 90 which can selectively make a changeover as to whether or not the excitation filter 121 is arranged on the white light emitted from the high-intensity light source 12.

When the filter-switching turret 90 is operated so as to arrange the excitation filter 121 on the white light and the power turret 60 is operated so as to arrange the tube lens 50A on which the fluorescence filter 171 is provided on the return light (see FIG. 4), the excitation light, which is obtained by the passage through the excitation filter 121, passes through the objective lens 40 via the mirror 20 and the beam splitter 30 so that the workpiece W is irradiated with the excitation light. On the workpiece W irradiated with the excitation light, the fluorescence according to the thickness of the fluorescent material formed on the workpiece W is emitted, and the irradiated excitation light is reflected. Return light including the fluorescence and the excitation light from the workpiece W passes through the fluorescence filter 171, through which only the fluorescence transmits, via the objective lens 40 and the beam splitter 30. The fluorescence passing through the fluorescence filter 171 passes through the tube lens 50A, and enters the CCD camera 70.

On the other hand, when the filter-switching turret 90 is operated so as not to arrange the excitation filter 121 on the white light and the power turret 60 is operated so as to arrange the tube lens 50 (e.g., the tube lens 50B) on which the fluorescence filter 171 is not provided on the return light, the workpiece W is irradiated directly with the white light emitted from the high-intensity light source 12. Further, the return light from the workpiece W passes through the tube lens 50B to enter the CCD camera 70 as unchanged, since the fluorescence filter 171 is not present on the return light from the workpiece W.

As described above, the optical measuring device 4 according to the fourth embodiment further includes the filter-switching turret 90 which is arranged between the white light source (high-intensity light source 12) and the objective lens 40 and which can selectively make a changeover as to whether or not the excitation filter 121, through which only the excitation light having a wavelength for making the fluorescence emitted from the workpiece W transmits, is arranged on the white light emitted from the high-intensity light source 12. Moreover, the optical measuring device 4 according to the fourth embodiment uses as the white light source the light source which emits the white light including the excitation light, and uses as the special filter the fluorescence filter 171 through which only the fluorescence emitted from the workpiece W out of the return light transmits. The objective lens 40 allows the passage of the white light or excitation light passing through the filter-switching turret 90, out of the white light emitted from the high-intensity light source 12.

With this configuration, not only the visual observation but also the fluorescent observation can be made according to the switching operation of the excitation filter 121 by the filter-switching turret 90 and the switching operation of the tube lens 50 by the power turret 60. Therefore, an IC wafer using a solder resist can be inspected, and a biological tissue or cell stained with a fluorescent pigment can be observed, for example.

(Fifth Embodiment)

A configuration will firstly be described. For simplifying the description, the components same as those in the first to fourth embodiments are denoted by the same numerals, and the description will not be repeated.

Figure 5A:
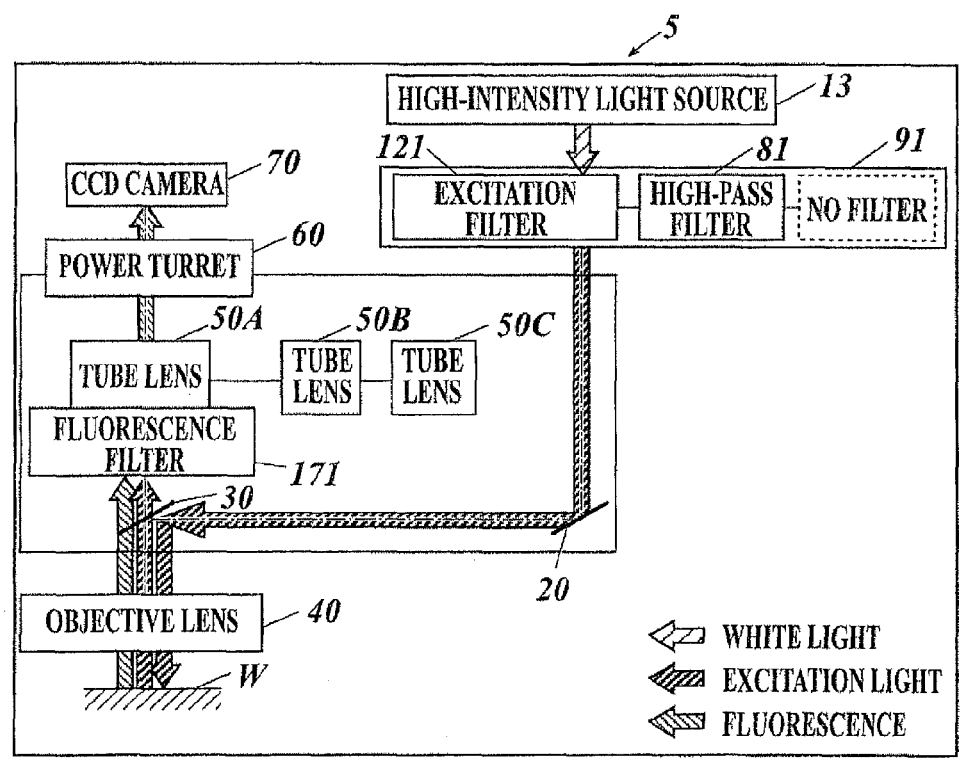
FIG. 5A is a schematic view illustrating a configuration of an optical measuring device according to a fifth embodiment.
Figure 5B:
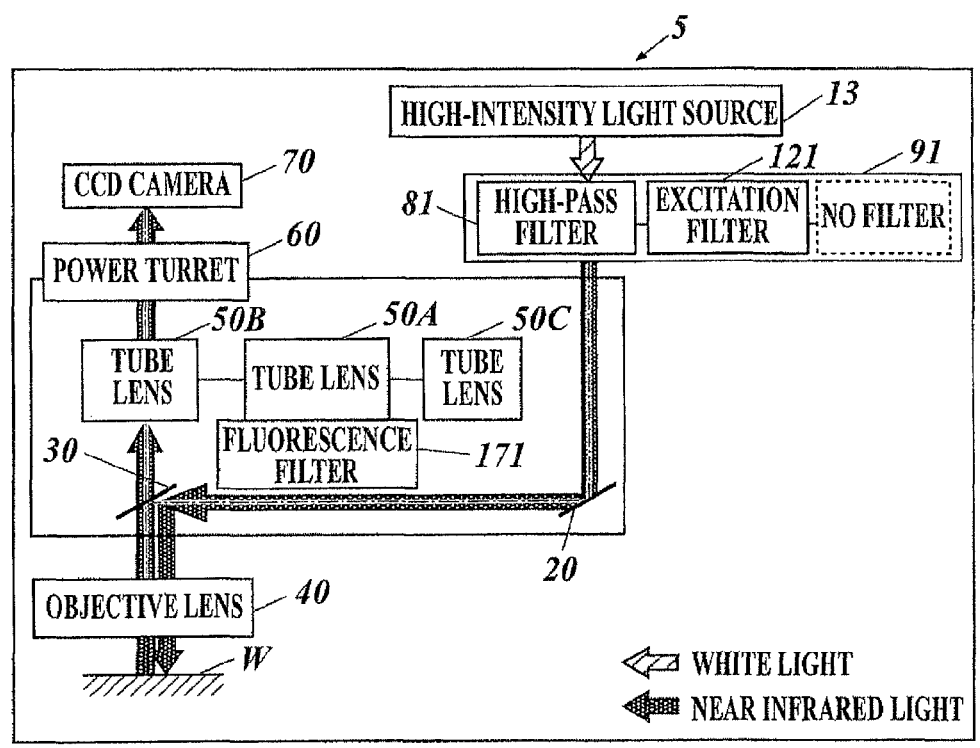
FIG. 5B is a schematic view illustrating the configuration of the optical measuring device according to the fifth embodiment.

An optical measuring device 5 according to a fifth embodiment includes, as illustrated in FIGS. 5A and 5B, a high-intensity light source 13, a filter-switching turret 91, a mirror 20, a beam splitter 30, an objective lens 40, tube lenses 50A, 50B, and 50C, a fluorescence filter 171, a power turret 60, and a CCD camera 70.

The high-intensity light source 13 is a wideband light source composed of a halogen, discharge lamp, or light-emitting diode, for example, and generates and emits high-intensity white light including near infrared light and excitation light. With the white light emitted from the high-intensity light source 13, the filter-switching turret 91 arranged below the high-intensity light source 13 in the vertical direction is irradiated.

The filter-switching turret 91 is a turret which can selectively make a changeover as to whether one of the excitation filter 121 through which only the excitation light having a wavelength for making the fluorescence emitted from the workpiece W transmits, and the high-pass filter 81 through which only the near infrared light transmits, is arranged on the white light emitted from the high-intensity light source 13, or neither of them is arranged. It serves as a filter-switching mechanism.

An operation will next be described.

The optical measuring device 5 has the filter-switching turret 91 which can selectively make a changeover as to whether one of the excitation filter 121 and the high-pass filter 81 is arranged on the white light emitted from the high-intensity light source 13, or neither of them is arranged.

When the filter-switching turret 91 is operated so as to arrange the excitation filter 121 on the white light and the power turret 60 is operated so as to arrange the tube lens 50A, on which the fluorescence filter 171 is provided, on the return light (see FIG. 5A), the excitation light, which is obtained by the passage through the excitation filter 121, passes through the objective lens 40 via the mirror 20 and the beam splitter 30, so that the workpiece W is irradiated with the excitation light. On the workpiece W irradiated with the excitation light, the fluorescence according to the thickness of the fluorescent material formed on the workpiece W is emitted, and the irradiated excitation light is reflected. The return light including the fluorescence and the excitation light from the workpiece W passes through the fluorescence filter 171, through which only the fluorescence transmits, via the objective lens 40 and the beam splitter 30. The fluorescence passing through the fluorescence filter 171 passes through the tube lens 50A, and enters the CCD camera 70.

When the filter-switching turret 91 is operated so as to arrange the high-pass filter 81 on the white light and the power turret 60 is operated so as to arrange the tube lens 50 (e.g., the tube lens 50B), on which the fluorescence filter 171 is not provided, on the return light (see FIG. 5B), the near infrared light obtained by the passage through the high-pass filter 81 passes through the objective lens 40 via the mirror 20 and the beam splitter 30 so that the workpiece W is irradiated with the near infrared light. The near infrared light with which the workpiece W is irradiated passes through the surface of the workpiece W, is reflected by the not-illustrated wiring, and then passes through the tube lens 50B via the objective lens 40 and the beam splitter 30, thereby entering the CCD camera 70.

When the filter-switching turret 91 is operated so as to arrange neither the excitation filter 121 nor the high-pass filter 81 on the white light, and the power turret 60 is operated so as to arrange the tube lens 50 (e.g., the tube lens 50B), on which the fluorescence filter 171 is not provided, on the return light, the workpiece W is irradiated directly with the white light emitted from the high-intensity light source 13. Further, the return light from the workpiece W passes through the tube lens 50B to enter the CCD camera 70 as unchanged, since the fluorescence filter 171 is not present on the return light from the workpiece W.

The optical measuring device 5 according to the fifth embodiment employs the light source, as the white light source (high-intensity light source 13), which emits the white light including the excitation light and the near infrared light. The filter-switching turret 91 can selectively make a changeover as to whether one of the excitation filter 121 through which only the excitation light having the wavelength for making the fluorescence emitted from the workpiece W transmits, and the high-pass filter 81 through which only the near infrared light transmits, is arranged on the white light emitted from the high-intensity light source 13, or neither of them is arranged. The objective lens 40 allows the passage of the white light, near infrared light, or excitation light, passing through the filter-switching turret 91, out of the white light emitted from the high-intensity light source 13.

With this configuration, not only the visual observation but also the fluorescent observation or the near infrared observation can be made according to the filter switching operation by the filter-switching turret 91 and the switching operation of the tube lens 50 by the power turret 60. Therefore, an IC wafer using a solder resist can be inspected, and a biological tissue or cell stained with a fluorescent pigment can be observed, a circuit board using a thin material such as silicon and a film can be checked, and a vein authentication to be utilized for security can be performed, for example.

(Modification of Fifth Embodiment)

A configuration will firstly be described. For simplifying the description, the components same as those in the first to fifth embodiments are denoted by the same numerals, and the description will not be repeated.

Figure 6A:
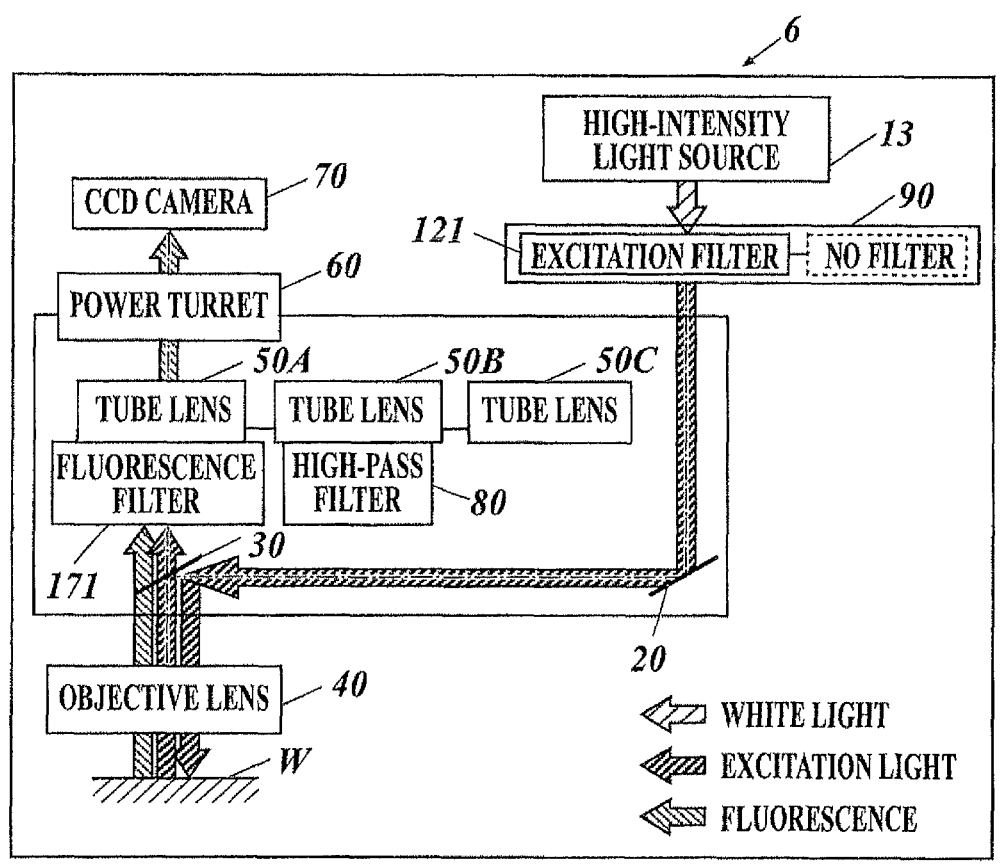
FIG. 6A is a schematic view illustrating a configuration of an optical measuring device according to modification of the fifth embodiment.
Figure 6B:
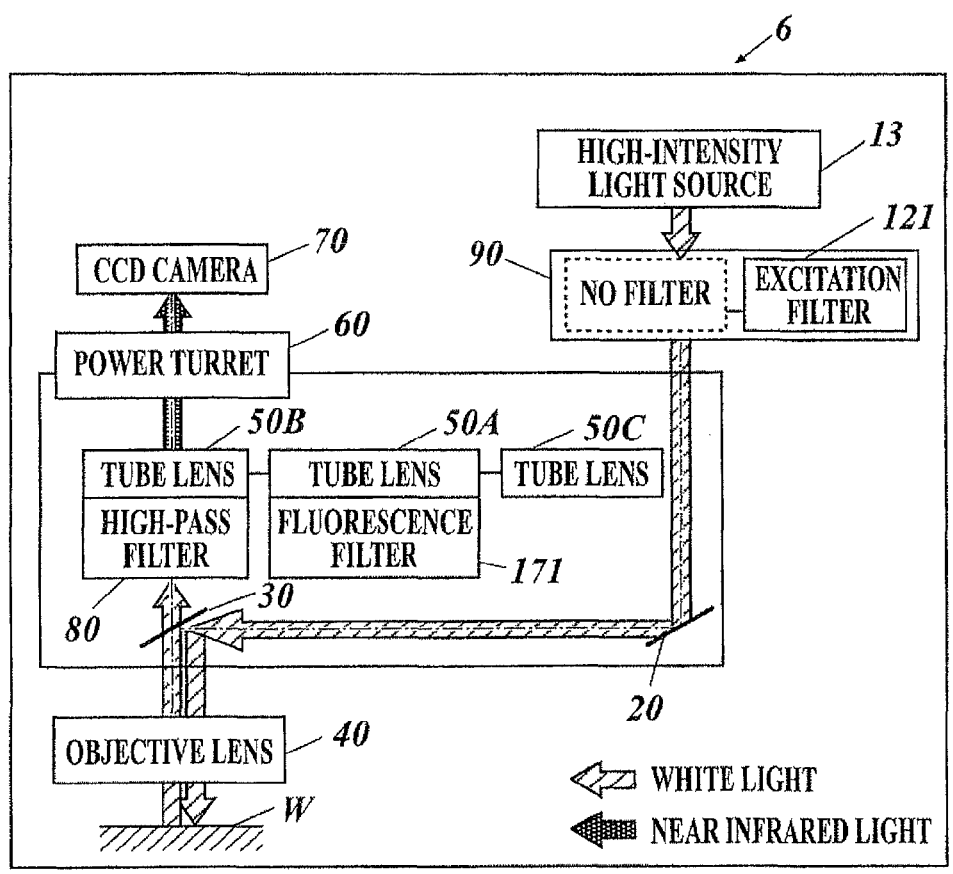
FIG. 6B is a schematic view illustrating the configuration of the optical measuring device according to the modification of the fifth embodiment.
Figure 7:
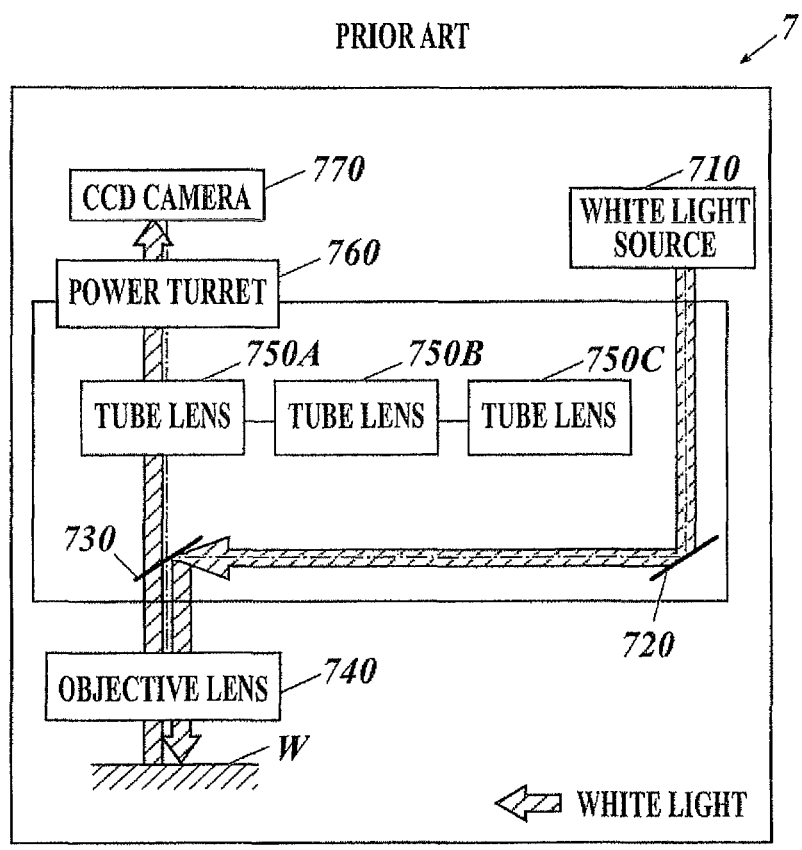
FIG. 7 is a schematic view illustrating a configuration of a conventional optical measuring device.
Figure 8:
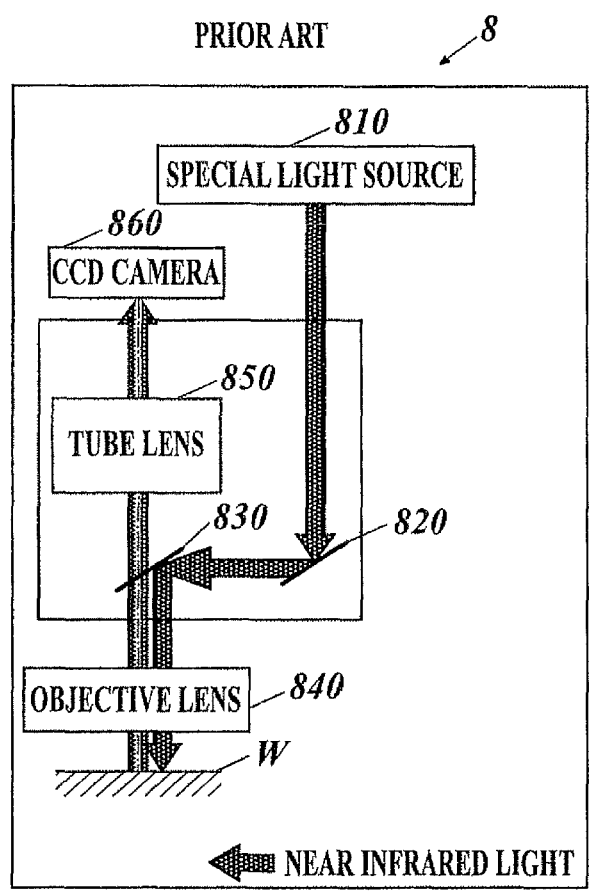
FIG. 8 is a schematic view illustrating a configuration of an optical measuring device for near-infrared observation.
Figure 9:
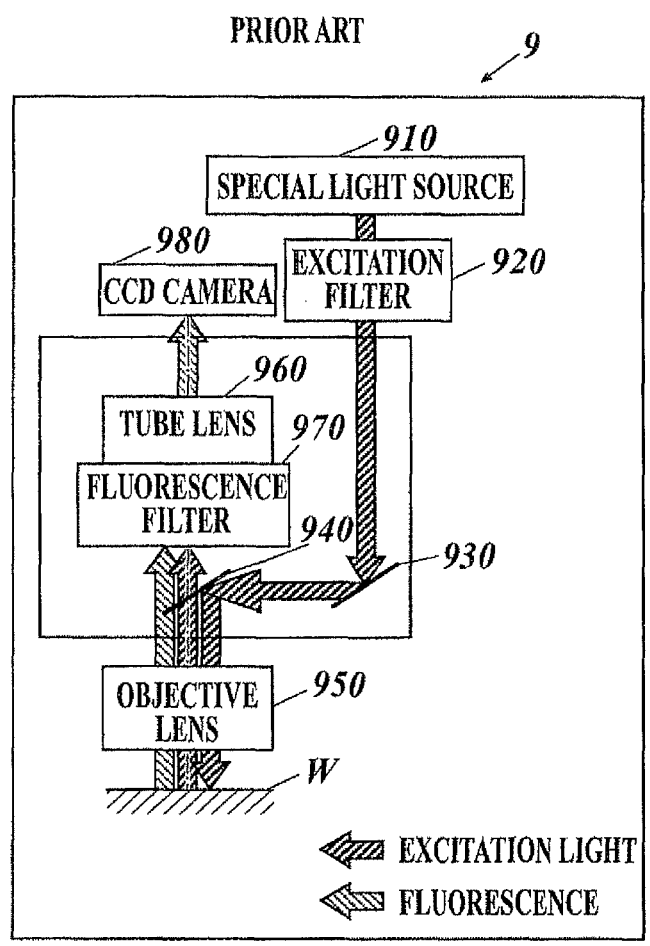
FIG. 9 is a schematic view illustrating a configuration of a conventional optical measuring device for fluorescent observation.

An optical measuring device 6 according to a modification of the fifth embodiment includes, as illustrated in FIGS. 6A and 6B, a high-intensity light source 13, a filter-switching turret 90, a mirror 20, a beam splitter 30, an objective lens 40, tube lenses 50A, 50B, and 50C, a fluorescence filter 171, a high-pass filter 80, a power turret 60, and a CCD camera 70.

It is different from the fifth embodiment in which the high-pass filter 80 is provided to the tube lens 50B, not in the filter-switching turret 90.

An operation will next be described.

The optical measuring device 6 has the filter-switching turret 90 which can selectively make a changeover as to whether or not the excitation filter 121 is arranged on the white light emitted from the high-intensity light source 13.

When the filter-switching turret 90 is operated so as to arrange the excitation filter 121 on the white light and the power turret 60 is operated so as to arrange the tube lens 50A, on which the fluorescence filter 171 is provided, on the return light (see FIG. 6A), the excitation light, which is obtained by the passage through the excitation filter 121, passes through the objective lens 40 via the mirror 20 and the beam splitter 30, so that the workpiece W is irradiated with the excitation light. On the workpiece W irradiated with the excitation light, the fluorescence according to the thickness of the fluorescent material formed on the workpiece W is emitted, and the irradiated excitation light is reflected. The return light including the fluorescence and the excitation light from the workpiece W passes through the fluorescence filter 171, through which only the fluorescence transmits, via the objective lens 40 and the beam splitter 30. The fluorescence passing through the fluorescence filter 171 passes through the tube lens 50A, and enters the CCD camera 70.

When the filter-switching turret 90 is operated so as not to arrange the excitation filter 121 on the white light and the power turret 60 is operated so as to arrange the tube lens 50B, on which the high-pass filter 80 is provided, on the return light (see FIG. 6B), the high-intensity white light emitted from the high-intensity light source 13 and including the near infrared light passes through the objective lens 40 via the mirror 20 and the beam splitter 30 so that the workpiece W is irradiated with the high-intensity white light. The near infrared light included in the white light, with which the workpiece W is irradiated, passes through the surface of the workpiece W and is reflected by the not-illustrated wiring. The return light from the workpiece W passes through the high-pass filter 80, through which only the near infrared light transmits, via the objective lens 40 and the beam splitter 30. The near infrared light passing through the high-pass filter 80 passes through the tube lens 50B to enter the CCD camera 70.

When the filter-switching turret 90 is operated so as not to arrange the excitation filter 121 on the white light and the power turret 60 is operated so as to arrange the tube lens 50 (e.g., the tube lens 50C), on which the fluorescence filter 171 and the high-pass filter 80 are not provided, on the return light, the workpiece W is irradiated directly with the white light emitted from the high-intensity light source 13. Further, the return light from the workpiece W passes through the tube lens 50C to enter the CCD camera 70 as unchanged, since the fluorescence filter 171 or the high-pass filter 80 is not present on the return light from the workpiece W.

The optical measuring device 6 according to the modification of the fifth embodiment employs the light source, as the white light source (high-intensity light source 13), which emits the white light including the excitation light and the near infrared light. The number of the tube lenses 50 is at least three or more, wherein one (e.g., the tube lens 50B) of the tube lenses 50 on which the fluorescence filter 171 is not provided has mounted thereon the high-pass filter 80 through which only the near infrared light transmits.

With this configuration, not only the visual observation but also the fluorescent observation or the near-infrared observation can be made according to the switching operation of the excitation filter 121 by the filter-switching turret 90 and the switching operation of the tube lens 50 by the power turret 60. Therefore, an IC wafer using a solder resist can be inspected, a biological tissue or cell stained with a fluorescent pigment can be observed, a circuit board using a thin material such as silicon and a film can be checked, and a vein authentication to be utilized for security can be performed, for example.

Although the embodiments according to the present invention have been described above, the present invention is not limited to the above-mentioned embodiments, and various modifications are possible without departing from the scope of the present invention.

For example, in the above-mentioned embodiments, the fluorescence filter and the high-pass filter are provided between the tube lens and the objective lens. However, the present invention is not limited thereto. For example, they may be provided between the tube lens and the CCD camera.

Various modifications are also possible without departing from the scope of the present invention for the detailed configurations and detailed operations of the components constituting the optical measuring device.

As described above, according to the embodiment of the present invention, there is provided an optical measuring device including: a visual observation section for performing a visual observation of a measurement object; and a special observation section for performing a special observation of the measurement object, wherein the visual observation section includes: a white light source which emits white light; a first objective lens arranged between the white light source and the measurement object, through which lens the white light emitted from the white light source and return light from the measurement object transmit; a plurality of tube lenses which change a magnification of the return light passing through the first objective lens to a predetermined magnification; and a lens switching mechanism which can selectively switch the tube lenses so as to select one of the tube lenses which is to be arranged on the return light, and wherein the special observation section includes: a special light source which emits special light; and a second objective lens arranged between the special light source and the measurement object, through which lens the special light emitted from the special light source and return light from the measurement object transmit.

Preferably, the special light is near infrared light.

Preferably, the optical measuring further includes: an excitation filter arranged between the special light source and the second objective lens, through which filter only excitation light having a wavelength for making a fluorescence emitted from the measurement object transmits; and a fluorescence filter through which only the fluorescence emitted from the measurement object, out of the return light passing through the second objective lens, transmits, and the special light is excitation light, and the excitation light passing through the excitation filter, out of the excitation light emitted from the special light source, transmits through the second objective lens.

Moreover, according to the embodiment of the present invention, there is provided an optical measuring device including: a white light source which emits white light including special light; an objective lens arranged between the white light source and a measurement object, through which lens the white light emitted from the white light source and return light from the measurement object transmit; a plurality of tube lenses which change a magnification of the return light passing through the objective lens to a predetermined magnification; a special filter provided on one of the tube lenses, through which filter only predetermined light transmits; and a lens switching mechanism which can selectively switch the tube lenses so as to select one of the tube lenses which is to be arranged on the return light.

Preferably, the special light is near infrared light, and the special filter is a near-infrared filter through which only the near infrared light transmits.

Preferably, the optical measuring device further includes a filter-switching mechanism which is arranged between the white light source and the objective lens, and which can selectively make a changeover as to whether an excitation filter through which only excitation light having a wavelength for making fluorescence emitted from the measurement object is arranged on the white light emitted from the white light source or not, the special light is excitation light, the white light or the excitation light passing through the filter-switching mechanism, out of the white light emitted from the white light source, transmits through the objective lens, and the special filter is a fluorescence filter through which only the fluorescence emitted from the measurement object, out of the return light, transmits.

Preferably, the special light includes near infrared light, the filter-switching mechanism can selectively make a changeover as to whether one of the excitation filter and a near-infrared filter through which only the near infrared light transmits is arranged on the white light emitted from the white light source, or neither the excitation filter nor the near-infrared filter is arranged, and the white light, the near infrared light, or the excitation light, passing through the filter-switching mechanism, out of the white light emitted from the white light source, transmits through the objective lens.

Preferably, the special light includes near infrared light, the number of the tube lenses is at least three or more, and the near-infrared filter through which only the near infrared light transmits is provided to one of the tube lenses on which the fluorescence filter is not provided.

As described above, since the present invention includes the visual observation section for the visual observation of the measurement object, and the special observation section for the special observation of the measurement object, not only the visual observation but also the near-infrared observation or the fluorescent observation can be made to the measurement object.

The entire disclosure of Japanese Patent Application No. 2010-281102 filed on Dec. 17, 2010, including specification, claims, drawings and abstract are incorporated herein by reference in its entirety.

What is claimed is:

1. An optical measuring device comprising:
    a white light source which emits white light including special light;
    an objective lens arranged between the white light source and a measurement object, through which lens the white light emitted from the white light source and return light from the measurement object transmit;
    a plurality of tube lenses which change a magnification of the return light passing through the objective lens to a predetermined magnification;
    a special filter provided on only one of the tube lenses, through which filter only predetermined light transmits; and
    a lens switching mechanism which can selectively switch the tube lenses so as to select one of the tube lenses which is to be arranged on the return light.

2. The optical measuring device according to claim 1, wherein the special light is near infrared light, and wherein the special filter is a near-infrared filter through which only the near infrared light transmits.

3. The optical measuring device according to claim 1, further comprising:
    a filter-switching mechanism which is arranged between the white light source and the objective lens, and which can selectively make a changeover as to whether an excitation filter through which only excitation light having a wavelength for making a fluorescence emitted from the measurement object is arranged on the white light emitted from the white light source or not,
    wherein the special light is excitation light,
    wherein the white light or the excitation light passing through the filter-switching mechanism, out of the white light emitted from the white light source, transmits through the objective lens, and
    wherein the special filter is a fluorescence filter through which only the fluorescence emitted from the measurement object, out of the return light, transmits.

4. The optical measuring device according to claim 3,
    wherein the special light includes near infrared light,
    wherein the filter-switching mechanism can selectively make a changeover as to whether one of the excitation filter and a near-infrared filter through which only the near infrared light transmits is arranged on the white light emitted from the white light source, or neither the excitation filter nor the near-infrared filter is arranged, and wherein the white light, the near infrared light, or the excitation light, passing through the filter-switching mechanism, out of the white light emitted from the white light source, transmits through the objective lens.

5. The optical measuring device according to claim 3, wherein the special light includes near infrared light, and wherein the number of the tube lenses is at least three or more, and a near-infrared filter through which only the near infrared light transmits is provided to one of the tube lenses on which the fluorescence filter is not provided.

6. The optical measuring device according to claim 1, further comprising a filter other than the special filter provided on at least one of the other tube lenses, through which filter light other than the predetermined light transmits.

* * * * *